US008244365B2

(12) United States Patent
Dijk et al.

(10) Patent No.: US 8,244,365 B2
(45) Date of Patent: Aug. 14, 2012

(54) SIMULTANEOUS DELIVERY OF ELECTRICAL AND ACOUSTICAL STIMULATION IN A HEARING PROSTHESIS

(75) Inventors: Bastiaan van Dijk, Mechelen (BE); Ibrahim Bouchataoui, Mechelen (BE); Mark Majoral, Brussels (BE); Ernst von Wallenberg, Muelheim (DE); Christopher J. James, Toulouse (FR); Matthijs Killian, Mechelen (BE)

(73) Assignee: Cochlear Limited, Macquarie University, NSW (AU)

( * ) Notice: Subject to any disclaimer, the term of this patent is extended or adjusted under 35 U.S.C. 154(b) by 1789 days.

(21) Appl. No.: 11/434,929

(22) Filed: May 17, 2006

(65) Prior Publication Data

US 2006/0287690 A1   Dec. 21, 2006

Related U.S. Application Data

(63) Continuation-in-part of application No. 11/125,334, filed on May 10, 2005, now Pat. No. 8,086,319.

(30) Foreign Application Priority Data

| May 10, 2004 | (AU) | 2004902462 |
| May 10, 2005 | (AU) | 2005201999 |
| Aug. 17, 2005 | (AU) | 2005203696 |

(51) Int. Cl.
  *A61N 1/08* (2006.01)
(52) U.S. Cl. ............ 607/56; 607/55; 607/57; 607/136; 607/137; 600/559; 623/10

(58) Field of Classification Search .................. 600/559; 623/10; 607/55–57, 136–137
See application file for complete search history.

(56) References Cited

U.S. PATENT DOCUMENTS

| 3,819,875 | A | | 6/1974 | Velmans |
| 4,261,372 | A | | 4/1981 | Hansen et al. |
| 4,487,210 | A | | 12/1984 | Knudsen et al. |
| 4,532,930 | A | | 8/1985 | Crosby et al. |
| 5,143,090 | A | | 9/1992 | Dutcher et al. |
| 5,594,174 | A | * | 1/1997 | Keefe .............................. 73/585 |
| 5,626,629 | A | | 5/1997 | Faltys et al. |
| 5,758,651 | A | | 6/1998 | Nygard et al. |
| 5,776,179 | A | * | 7/1998 | Ren et al. ...................... 607/137 |

(Continued)

FOREIGN PATENT DOCUMENTS

AU   2005201999   11/2005

(Continued)

OTHER PUBLICATIONS

Patent Cooperation Treaty, "International Search Report," issued by the International Searching Authority in connection with PCT application No. PCT/AU2003/000828, mailed Sep. 2, 2003 (5 pages).

(Continued)

*Primary Examiner* — Carl H Layno
*Assistant Examiner* — Natasha Patel
(74) *Attorney, Agent, or Firm* — Kilpatrick, Townsend & Stockton, LLP.

(57) ABSTRACT

A bimodal hearing prosthesis configured to deliver electrical and acoustic stimulation to a recipient such that a frequency range of a received sound that is represented by the electrical stimulation is perceived simultaneously with the frequency range of the received sound that is represented by the acoustic stimulation.

28 Claims, 12 Drawing Sheets

U.S. PATENT DOCUMENTS

| | | | |
|---|---|---|---|
| 5,792,072 A * | 8/1998 | Keefe | 600/559 |
| 5,922,017 A | 7/1999 | Bredberg et al. | |
| 5,991,663 A | 11/1999 | Irlicht et al. | |
| 6,070,105 A | 5/2000 | Kuzma | |
| 6,119,044 A | 9/2000 | Kuzma | |
| 6,157,861 A | 12/2000 | Faltys et al. | |
| 6,163,729 A | 12/2000 | Kuzma | |
| 6,231,604 B1 * | 5/2001 | von Ilberg | 623/10 |
| 6,259,951 B1 | 7/2001 | Kuzma et al. | |
| 6,308,101 B1 | 10/2001 | Faltys et al. | |
| 6,415,185 B1 * | 7/2002 | Maltan | 607/57 |
| 6,487,453 B1 | 11/2002 | Kuzma et al. | |
| 6,498,954 B1 | 12/2002 | Kuzma et al. | |
| 6,556,870 B2 * | 4/2003 | Zierhofer et al. | 607/137 |
| 6,628,991 B2 | 9/2003 | Kuzma et al. | |
| 6,754,537 B1 * | 6/2004 | Harrison et al. | 607/57 |
| 6,889,094 B1 | 5/2005 | Kuzma et al. | |
| 6,915,166 B1 | 7/2005 | Stecker et al. | |
| 2004/0133250 A1 | 7/2004 | Ball et al. | |
| 2004/0225336 A1 | 11/2004 | Milojevic et al. | |
| 2005/0101878 A1 | 5/2005 | Daly et al. | |
| 2005/0245991 A1 | 11/2005 | Faltys et al. | |
| 2005/0256561 A1 | 11/2005 | Gantz et al. | |
| 2005/0261748 A1 | 11/2005 | van Dijk | |
| 2006/0287690 A1 | 12/2006 | Bouchataoui et al. | |
| 2007/0179566 A1 | 8/2007 | Gantz et al. | |
| 2007/0203557 A1 | 8/2007 | Gantz et al. | |

FOREIGN PATENT DOCUMENTS

| | | |
|---|---|---|
| AU | 2005203696 | 11/2005 |
| WO | 9631087 | 10/1996 |
| WO | 9726943 | 7/1997 |
| WO | 0069513 | 11/2000 |
| WO | 0071063 | 11/2000 |
| WO | WO 02/082982 | 10/2002 |
| WO | WO-02082982 | 10/2002 |
| WO | 2004004413 | 1/2004 |

OTHER PUBLICATIONS

Patent Cooperation Treaty, "International Preliminary Examination Report," issued by the International Searching Authority in connection with PCT application No. PCT/AU2003/000828, issued Oct. 8, 2004 (7 pages).

Gantz et al., "Combining Acoustic and Electrical Hearing," pp. 1726-1730, The Laryngoscope, Oct. 2003 (5 pages).

Written Opinion for PCT/AU03/00828, dated Oct. 16, 2003, 7 Pages.

* cited by examiner

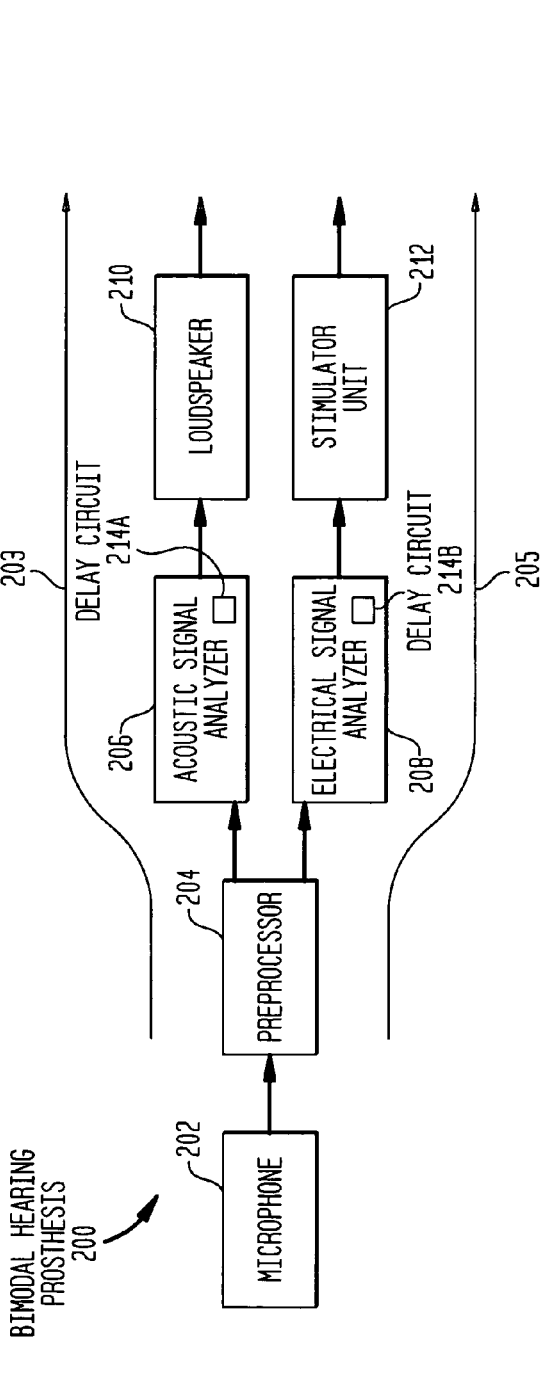
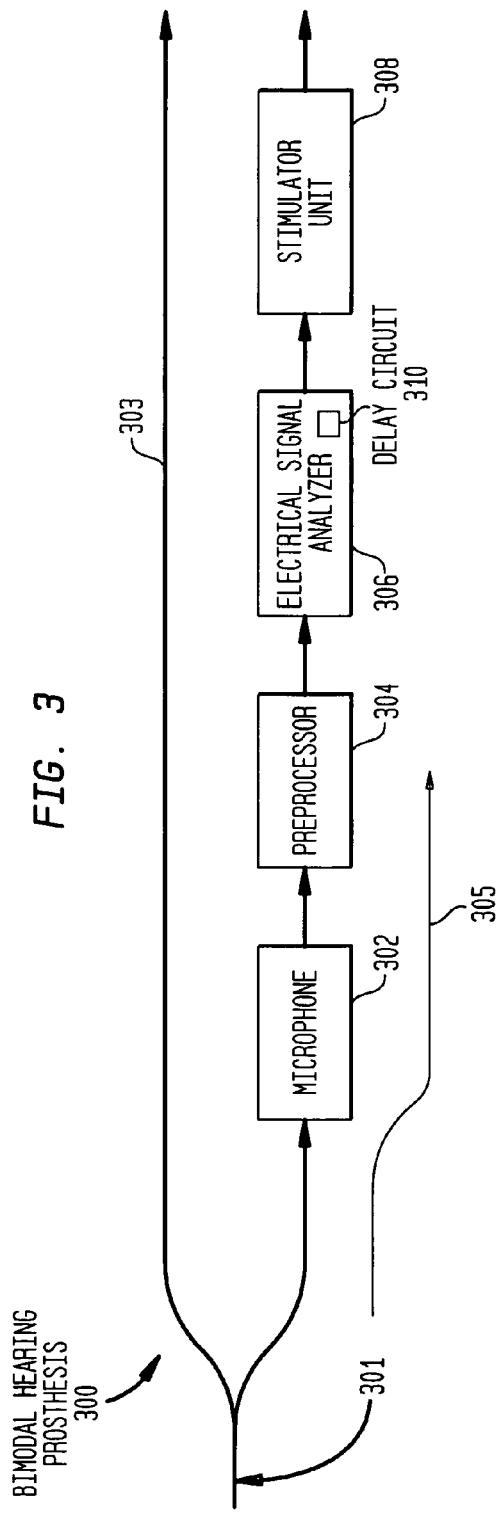

SIMULTANEOUS DELIVERY OF ELECTRICAL AND ACOUSTICAL STIMULATION IN A HEARING PROSTHESIS

CROSS-REFERENCE TO RELATED APPLICATIONS

The present application is a continuation-in-part of U.S. patent application Ser. No. 11/125,334 now U.S. Pat. No. 8,086,319, filed May 10, 2005, which claims priority from Australian Provisional Patent Application No. 2004902462, filed May 10, 2004. The present application further claims priority from Australian Patent Application No. 2005203696, filed Aug. 17, 2005, which claims priority from Australian Patent Application No. 2005201999, filed May 10, 2005. The entire disclosure and contents of the above-identified applications are hereby incorporated by reference herein.

BACKGROUND

1. Field of the Invention

The present invention relates generally to hearing prostheses, and more particularly, to simultaneous delivery of electrical and acoustical stimulation in a hearing prosthesis.

2. Related Art

Hearing prostheses such as cochlear implants have been developed to assist people who are profoundly deaf or severely hearing impaired, by enabling them to experience a hearing sensation representative of the natural hearing sensation. For most such individuals the hair cells in the cochlea, which normally transduce acoustic signals into nerve impulses to be interpreted by the brain as sound, are absent or have been partially or completely destroyed. Cochlear implants bypass the cochlear hair cells to directly deliver electrical stimulation to the auditory nerve with this electrical stimulation being representative of the sound.

Cochlear implants have traditionally included external and internal components. A speech processor worn on the recipient's body detects external sounds using a microphone and converts the detected sounds into a coded signal utilizing an appropriate speech processing strategy.

This coded signal is then sent via a transcutaneous link to a receiver/stimulator unit implanted in the mastoid bone of the recipient. The receiver/stimulator unit processes the coded signal into a series of stimulation sequences which are then applied directly to the auditory nerve via an array of electrodes positioned within the cochlea, proximal to the modiolus of the cochlea. One such cochlear implant is set out in U.S. Pat. No. 4,532,930, the contents of which are hereby incorporated by reference herein.

With improvements in technology it is possible that the external speech processor and implanted stimulator unit may be combined to produce a totally implantable cochlear implant unit that is capable of operating, at least for a period of time, without the need for any external device. In such a device, a microphone may be implanted within the body of the recipient, for example in the ear canal or within the stimulator unit, and sound would be detected and directly processed by a speech processor within the stimulator unit, with the subsequent stimulation signals delivered without the need for any transcutaneous transmission of signals. Such a device would, however, still have the capability to communicate with an external device when necessary, particularly for program upgrades and/or implant interrogation, and to modify the operating parameters of the device.

Much effort has gone into developing stimulation strategies to provide for device customization to produce the best available percepts for the prosthesis recipient. Nevertheless it is acknowledged in the cochlear implant field that the percepts produced by pulsatile electrical stimulation often sound unnatural and somewhat harsh. Many recipients adapt to this sound and, after some time, even find it natural. This is not always the case, however, and some recipients may experience difficulties. For example, for some recipients having residual hearing, the expectation of harsh and/or unnatural sounding percepts produced by a cochlear implant has been less attractive than simply persisting with residual hearing, usually assisted by an acoustic hearing aid.

SUMMARY

A bimodal hearing prosthesis configured to deliver electrical and acoustic stimulation to a recipient such that a frequency range of a received sound that is represented by the electrical stimulation is perceived simultaneously with the frequency range of the received sound that is represented by the acoustic stimulation.

In one aspect of the invention, a method of electrically and acoustically stimulating a cochlea is disclosed. The method comprises: providing an acoustic signal delivery path to the cochlea; providing an electrical signal delivery path to the cochlea, for processing a first frequency sub-range of a detected sound signal for electric stimulation of the cochlea; and imposing a delay on at least one of the acoustic signal delivery path and the electrical signal delivery path, to provide for delivery of the electrical stimulation to the cochlea at a desired time relative to a time of arrival of acoustic stimuli at the cochlea.

BRIEF DESCRIPTION OF THE DRAWINGS

By way of example only, embodiments of the invention will be described with reference to the accompanying drawings, in which:

FIG. 2 is a block diagram of one embodiment of a bimodal hearing prosthesis for applying acoustic stimulation and electrical stimulation to a cochlea at a controlled time relative to each other;

FIG. 3 is a block diagram of another embodiment of a bimodal hearing prosthesis for applying electrical stimulation to a cochlea at a controlled time relative to normal acoustic stimulation;

DETAILED DESCRIPTION

Figure 1:
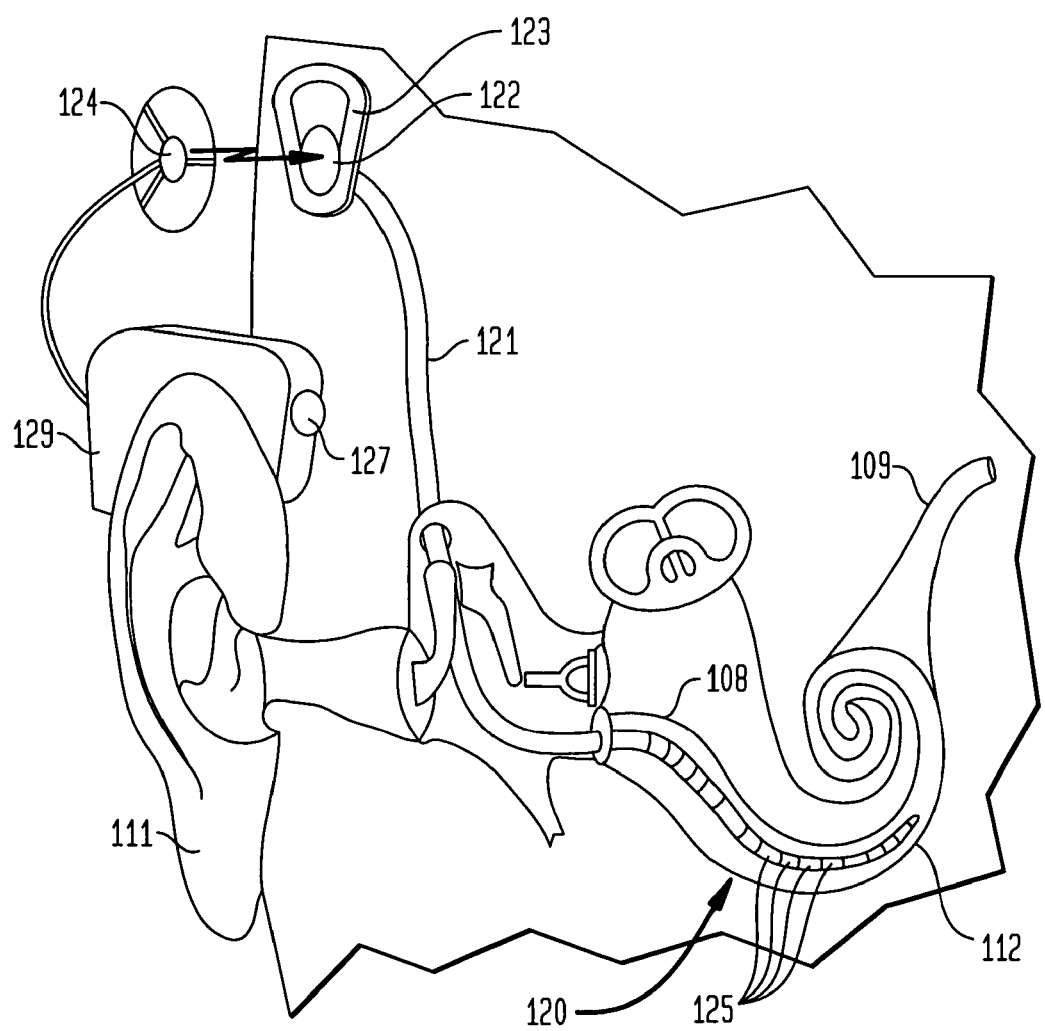
FIG. 1 is perspective view of an exemplary cochlear implant prosthesis in which embodiments of the present invention may be advantageously implemented.

Before describing the features of the present invention, it is appropriate to briefly describe the construction of a cochlear implant system with reference to FIG. 1.

Cochlear implants typically consist of two main components, an external component including a sound processor 129, and an internal component including an implanted receiver and stimulator unit 122. The external component also includes an on-board microphone 127. The sound processor 129 is, in this illustration, constructed and arranged so that it can fit behind the outer ear 111. Alternative versions may be worn on the body or it may be possible to provide a fully implantable system which incorporates the speech processor and/or microphone into the implanted stimulator unit. Attached to the sound processor 129 is a transmitter coil 124 which transmits electrical signals to the implanted receiver and stimulator unit 122 via an RF link.

The implanted component also includes a receiver coil 123 for receiving power and data from transmitter coil 124. A cable 121 extends from the implanted receiver and stimulator unit 122 to the cochlea 112 and terminates in an electrode array 120. The electrode array 120 comprises a plurality of electrodes 125. The signals thus received are applied by array 120 to the basilar membrane 108 thereby stimulating the auditory nerve 109. While the cochlea is generally spiral shaped as shown, it is convenient to describe electrode positions and the like as being "along" the cochlea between a basal end of the cochlea and an apical end of the cochlea as if the cochlea were unrolled to lie straight. The operation of such a device is described, for example, in U.S. Pat. No. 4,532,930.

Further, in certain embodiments, sound processor 129 may be connected to an ear mold (not shown) or other similar device, such as those commonly used with hearing aids, for delivery of acoustic signals to the implant recipient. As will be described in greater detail below, this permits such certain embodiments of sound processor 129 to simultaneously deliver both electrical stimuli via electrode array 120 and acoustic signals via a loudspeaker within sound processor 129.

Sound processor 129 of cochlear implant 100 may perform an audio spectral analysis of the acoustic signals to output channel amplitude levels. Sound processor 129 may also sort the output channel amplitude levels in order of magnitude, or flag the spectral maxima as used in the SPEAK strategy developed by Cochlear Ltd. Multi-channel adaptive processing may be applied, for example, by use of the adaptive dynamic range optimization (ADRO) technique set out in U.S. Pat. No. 6,731,767, which is hereby incorporated by reference herein.

With the continued improvement in surgical techniques, resulting in minimal or no damage to the internal structure of a recipient's ear, and the increase in performance of cochlear implants, more recipients have useful residual hearing capability. Aspects of the present invention provide for electrical and acoustic stimulation of the cochlea. Such bimodal stimulation takes advantage of the recipient's residual natural hearing capability, while supplementing that natural hearing with electrical stimuli to convey sound information which is only partially conveyed or is not conveyed by the natural hearing of the recipient.

The bimodal stimulation may be controlled by a speech processor having the ability to process detected sound to produce both electrical stimulations for application by an electrode array and acoustic stimulations for application by a hearing aid. Alternatively, bimodal stimulation of present invention may be controlled by a speech processor that produces electrical stimulation only, to be used in conjunction with acoustic stimulation that naturally enters the ear. Alternatively, a first speech processor for generating electrical stimulations may be used in conjunction with a second speech processor for producing acoustic stimulations.

Further, it is desirable to optimize the combination of electrical and acoustical stimulation in the fitting process, whether intra-operatively in the positioning of the electrode array, or post-operatively in establishing an optimal recipient map, or both. It may further be desirable to determine which electrodes are to be active and which are to remain inactive, to determine the frequency allocation of each active electrode so as to optimize the combinatory hearing, and to apply channel-specific gain to optimize the timing of delivery of stimuli by each active electrode.

FIG. 2 is a block diagram of one embodiment of a bimodal hearing prosthesis 200 capable of applying acoustic stimulation and electrical stimulation to a cochlea at a controlled time relative to each other. A microphone 202 detects sound signals and passes corresponding electrical signals to a preprocessor 204. Preprocessor 204 filters the electrical signals and passes a signal component in a first frequency sub-band to an electrical signal analyzer 208, and passes a signal component in a second frequency sub-band to an acoustic signal analyzer 206. In this embodiment the first frequency sub-band comprises a high frequency portion of the audible frequency spectrum, which corresponds to a basal region of a cochlea adjacent to which an electrode array has been positioned. The second frequency sub-band comprises a low frequency portion of the audible frequency spectrum, which corresponds to an apical region of the cochlea in which residual natural hearing of the cochlea has been retained.

Bimodal hearing prosthesis 200 of FIG. 2 further comprises a loudspeaker 210 for acoustically stimulating the cochlea, and a stimulator unit 212 for electrically stimulating the cochlea. Loudspeaker 210 may, for example, be any type of loudspeaker such as those commonly used with hearing aids. Further, any type of mechanism may be utilized to deliver acoustic sound from loudspeaker 210 to the implant receiver, such as, for example, an ear mold, an ear hook, etc.

In accordance with certain embodiments of the present invention, acoustic signal analyzer 204 and electrical signal analyzer 208 comprise respective delay circuits 214A and 214B, respectively, for delaying one or both of the electrical signals to ensure substantially simultaneous stimulation of the cochlea by loudspeaker 210 and the cochlear implant 212. Such delay circuits 214A and 214B may be any type of delay circuits now or later developed, and may be implemented in hardware, software or any combination thereof. For example, delay circuits may comprise one or more commercially available digital delay integrated chips or be implemented by software executing on a processor of signal analyzers 206 and/or 208, respectively. Or, for example, delay circuits for signal analyzers 206 and 208, respectively may be implemented by a common processor used in implanting both signal analyzers 206 and 208.

Substantial simultaneous stimulation of the cochlea is desirable so that the implant recipient does not perceive a delay between the two types of stimulations. Such a delay could be bothersome to the implant recipient and interfere with the enjoyment and/or effectiveness of the recipient's hearing. It should be noted that FIG. 2 is a simplified diagram provided for explanatory purposes. In actual implementations, bimodal hearing prosthesis 200 may include various other components along both the electrical signal delivery path 203 and acoustic signal delivery path 205, such as, for example, equalizers, etc.

FIG. 3 is a block diagram of an alternative embodiment of a bimodal hearing prosthesis 300 in which electrical stimulation is applied to a cochlea at a controlled time relative to normal acoustic stimulation. A sound signal 301 is detected by a microphone 302, and also passes along the natural acoustic delivery path 303 to the cochlea. Microphone 302 passes a corresponding electrical signal along electrical signal delivery path 305 to pre-processor 304, which in turn passes a pre-processed electrical signal to the electrical signal analyzer 306. Analyzer 306 passes signals to a stimulator unit 308 for electrical stimulation of the cochlea.

Analyzer 306 comprises a delay circuit 310 for delaying the electrical signal in order to ensure substantially simultaneous stimulation of the cochlea by stimulator unit 308 and the sound passing along acoustic delivery path 303.

Figure 4:
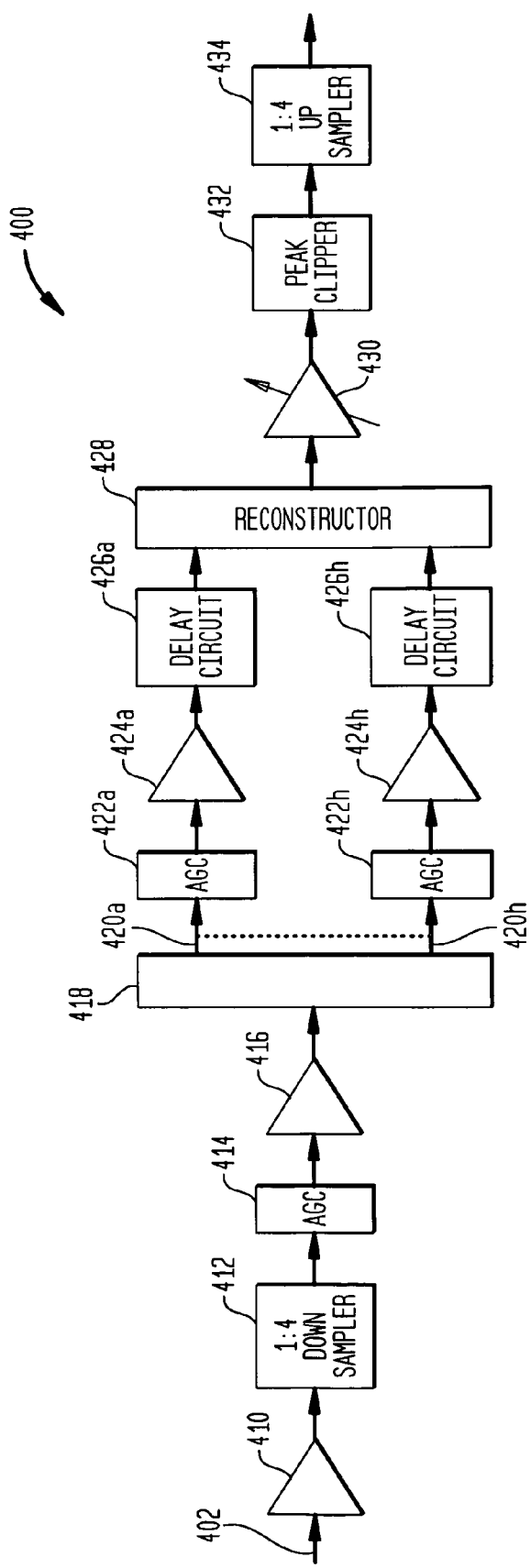
FIG. 4 is a circuit block diagram of a processing path through the acoustic signal analyzer illustrated in FIG. 2.

FIG. 4 is a circuit schematic of a processing path 400 through the acoustic signal analyzer of FIG. 2 (block 204) of a signal for acoustic stimulation of the cochlea. A sound signal is received by microphone 200 (FIG. 2) which generates a corresponding electrical signal that is pre-amplified, converted from analog to digital and passed through automatic sensitivity control circuitry in preprocessor 202 (FIG. 2). The resulting signal 402 is input to an acoustic gain amplifier 410, and then passed through a 1:4 down-sampler 412, an input automatic gain controller (AGC) 414 and an AGC gain 416. A filter bank 418 divides the signal into eight frequency bands 420a . . . 420h. Each frequency band 420 is processed by a respective AGC 422 and AGC gain 424. In accordance with embodiments of the present invention, each channel is then passed through an associated delay circuit 426, with each delay circuit 426 applying a channel-specific delay. The channels are then reconstructed by a reconstructor 428, and passed through a volume control amplifier 430, a peak clipper 432 and a 1:4 up-sampler 434 before being passed to loudspeaker 206 (FIG. 2) for acoustic stimulation of the cochlea. Thus, in addition to processing path 400, an acoustic signal delivery path comprises the propagation path of the acoustic signal from the loudspeaker, through the outer ear and middle ear into the inner ear.

In addition to applying channel-specific delays along the acoustic signal delivery path, the electric signal analyzer of FIGS. 2 and 3 (blocks 208 and 306) may also be able to apply independent channel-specific delays using delay circuits. These channel-specific delays may be set such that selected low frequency electrical channels are delayed for a longer time than higher frequency electrical channels. Such an embodiment may be used to mimic the time taken for sound to travel from a basal region of the cochlea tonotopically corresponding to the high frequency channels to a more apical region of the cochlea tonotopically corresponding to the low frequency channels.

Embodiments of the present invention may further recognize that appropriate configuration of the delay can be assessed objectively without requiring subjective patient responses, by detecting a neural response evoked by acoustic and/or electrical stimulation. The sensing of the evoked neural response is preferably performed in accordance with the method set out in U.S. patent application Ser. No. 10/475,141 entitled "Method and Apparatus for Measurement of Evoked Neural Response," the contents of which are hereby incorporated by reference herein. By eliminating the need for subjective patient responses in determining the respective timing of delivery of acoustic and electrical stimuli, such embodiments may be particularly advantageous where the recipient is a young child unable to indicate subjective responses to cochlea stimuli.

Figure 5:
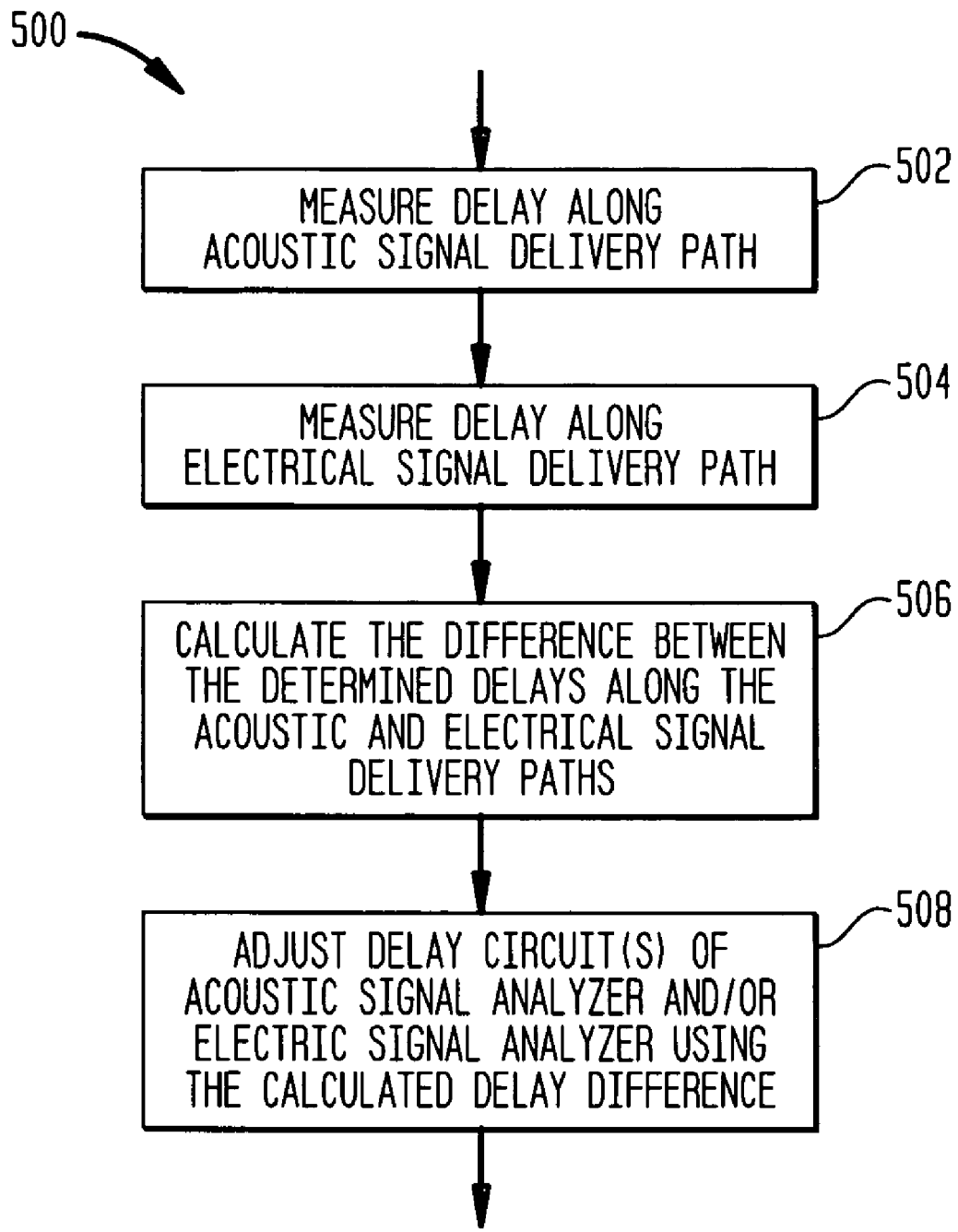
FIG. 5 is a flowchart of one embodiment of a method of measuring a difference in delay between an acoustic signal delivery path and the electrical signal delivery path.

FIG. 5 is a flowchart of one embodiment of a method of measuring a difference in delay between an acoustic signal delivery path and the electrical signal delivery path so that the difference in delays can be accounted for in order to ensure simultaneous delivery of stimulation. First, at block 502, the delay along the acoustic signal delivery path may be measured. This may be accomplished by generating an acoustic signal, preferably of short duration that is received by microphone 200 (or 302). The Electrically Evoked Compound Action Potentials (ECAP) caused by this acoustic signal may then be measured using a cochlear implant system, such as, for example, the cochlear implant system discussed in the above referenced U.S. patent application Ser. No. 10/475, 141. The difference in time between when the acoustic signal was generated and the time of the ECAP measurement can then be calculated to provide the effective delay along the acoustical signal delivery path. In one embodiment, the frequency for this audio signal may be chosen such that it will be delivered along the acoustic signal delivery path and not by the electrical signal delivery path. That is, the frequency of the audio signal may be elected so that it is included in the band of frequencies that will be provided via acoustic stimulation and not via electrical stimulation.

Next, at block 504 the effective delay of the signal along the electrical signal delivery path may be measured. This may be accomplished by generating an acoustic signal that is received by microphone 200 (or 302). The frequency for this acoustic signal is preferably selected so that this signal will be delivered via the electrical signal delivery path and not the acoustic signal delivery path (i.e., the implant recipient lacks normal hearing for this frequency). The ECAP resulting from this acoustic signal may then be measured. The difference in time between when the acoustic signal was generated and the time of the ECAP measurement can then be calculated to provide the effective delay along the electrical signal delivery path. The difference between the determined delays along the acoustic and electrical signal delivery paths may then be calculated at block 506. This difference may then be used at block 508 to adjust the delay circuits of the acoustic signal analyzer 204 and/or electrical signal analyzer 208 or 306 to ensure that signals traveling along these two paths are delivered simultaneously.

In implementing embodiments of the present invention, it is desirable to implant the electrode array without affecting the residual hearing, whether by adversely influencing the fluid dynamics of the inner ear or by damaging inner ear structures. The risk of such damage, and in particular the likelihood of perforating of the basilar membrane which would destroy all remaining hearing, increases with insertion depth of the electrode array. Damage to the lateral or modiolar wall of the cochlea may also occur during implantation. A partial insertion of the array reduces the risk of such damage. On the other hand, use of suitable surgical implantation techniques and suitable electrode arrays may enable complete insertion with an acceptable risk of such damage, in accordance with certain aspects of the present invention.

Further, it is desirable to optimize the combination of electrical and acoustical stimulation in the fitting process, whether intra-operatively in the positioning of the electrode array, or post-operatively in establishing an optimal patient map, or both. It may further be necessary to determine which electrodes are to be active and which are to remain inactive, and to determine the frequency allocation of each active electrode so as to optimize the combinatory hearing.

It should be appreciated that a recipient's residual hearing capability can be assessed objectively without requiring subjective recipient responses by detecting a neural response evoked by acoustic and/or electrical stimulation. For instance, an electrode of the electrode array may be used as a sense electrode for sensing an evoked neural response. The sensing of the evoked neural response is preferably performed in accordance with the method set out in International Patent Publication Number WO 02/082,982, the contents of which are hereby incorporated by reference herein. By eliminating the need for subjective recipient responses in determining a residual hearing capability, embodiments of the present invention enable intra-operative determination of residual hearing, thus providing for the ability to intra-operatively determine optimal insertion depth or position of the electrode array. Further, measurement of the evoked neural response can be used to objectively post-operatively optimize the electrode mapping configuration for each electrode position along the cochlea, for a recipient with residual hearing.

Such embodiments of the present invention also recognize the difficulty in precisely mapping a particular frequency to a position on the cochlea corresponding to that frequency. That is, it is difficult to accurately define an appropriate insertion depth for a partial insertion of an electrode array based on a previously measured audiogram of the cochlea. Further, it is difficult to know an actual depth to which an array has been inserted, even when imaging the array and cochlea during insertion, for example by X-ray.

Similarly, once an array is inserted, whether partially or fully, it is difficult to accurately map frequency bands to electrodes to correspond to a position of each electrode along the cochlea. This problem is compounded by the fact that an acoustic stimulation position for a particular frequency may not necessarily correspond to an appropriate electrical stimulation position for that frequency. Incorrect array positioning and/or incorrect frequency allocation to electrodes will lead to shifted frequency delivery to the cochlea, and can lead to contraposition of the acoustically delivered frequency range against the electrically delivered frequency range.

However, by sensing the evoked neural response, such embodiments of the invention enable such frequency vs. position determinations to be carried out with reference to an actual position of the sense electrode.

Such objective measurement of the residual hearing capability of the cochlea may further be particularly advantageous where the recipient is a young child unable to indicate subjective responses to auditory stimuli, and thus unable to assist in measurement of an audiogram. A cut-off frequency at the limit of the residual hearing is preferably also determined with reference to objective neural measurements rather than a subjective audiogram. One reason to prefer objective measurement of the cut-off frequency is that the limited frequency resolution of a partially damaged cochlea raises the possibility that a stimuli of a first frequency will produce a subjective response in the patient, but only because that frequency raises a neural response in auditory nerves which are typically considered to relate to a different (usually lower) frequency. In such circumstances, the auditory nerve relating to the first frequency may be inoperable, yet stimulation at that frequency causes a subjective response, which may lead to an incorrect conclusion that the auditory nerves relating to the first frequency are operable. To the contrary, an objective interactive measurement of a neural response may avoid this problem. Additionally or alternatively, use of the TEN test developed by Moore et al (Moore, B. C. J., Glasberg, B. R., Stone, M. A., 2004, *A new version of the TEN test with calibrations in dB* HL. Ear Hear. 25, 478-487) may be used to accurately measure the position of residual hearing in the cochlea.

To obtain a detailed impression of the residual hearing capability of the cochlea and of how electrical and acoustic stimulation will interact, several measurements of the neural response are preferably obtained. To address the localized sensitivity of the cochlea to electrical stimuli, the neural response evoked by an electrical stimulus at a specific location along the cochlea is preferably obtained, for a plurality of positions along the cochlea. Further, the neural response evoked by acoustic stimulation at specific frequencies is preferably determined by applying a short duration acoustic stimulus of specific frequency and using an electrode in a position tonotopically corresponding to that frequency to measure the neural response evoked by the acoustic stimulation, for a plurality of frequencies in the range audible to normal hearing. Additionally, the interaction between acoustic stimuli and electrical stimuli is preferably assessed by recording electrically evoked compound action potentials in the presence of acoustic masker stimuli, and also recording acoustically evoked compound action potentials in the presence of electrical masker stimuli. An appropriate electrical masker stimuli may comprise a forward masking paradigm, with a burst of electrical masker preceding the acoustical signal. An electrical masker stimuli may comprise a pulse burst at a rate equal to the mapping rate on a single electrode. An acoustic masker stimuli may comprise broadband or narrowband noise at high levels, with narrowband noise suitable for investigating tonotopic (frequency to location) characteristics of the cochlea.

It should be noted that, as explained by Fourier theory, there may be a conflict between generating both short duration signals and frequency specific signals. For example, the shortest acoustic signal, a click, has a broad spectrum and the sharpest frequency (a tone) has infinite duration. As noted above, it is preferable to measure ECAPs using short duration stimuli in order make it easier to synchronize the response with the acoustic signal. As such, the duration and frequency (or frequency band) of the signal are preferably chosen with this in mind. Options for generating acceptable short duration frequency specific signals for use in embodiments of the invention include, but are not limited to, using a band pass filtered click (i.e., filtering a click with a bandpass filter tuned to the desired frequency) or using a very short tone pip. These techniques are well known to those of skill in the art and are commonly used in clinical measurements such as electrocochleography (ECOG) measurements, measurements of compound action potentials with a needle electrode on the cochlear bone, and auditory brainstem response (ABR) measurement, such as ABR measurements where external scalp electrodes are used.

The amplitude of compound action potentials produced by acoustic stimuli and electrical stimuli are around the same order of magnitude and thus interfere in a measurable way. To provide for such measurements, a system could be used comprising a cochlear implant with neural response measurement and recordal capabilities, software to drive appropriate stimulus and measurement procedures, and an acoustic stimulator.

Features of another embodiment of the present invention are illustrated in FIGS. 6A to 6D. In this embodiment, an optimal insertion depth of an electrode array is intra-operatively determined. In recipients with residual hearing it is difficult to determine a suitable depth of insertion of the electrode array due to difficulties in precisely determining the location of the electrode, or due to difficulties in precisely determining the location of surviving neural elements that still can respond to acoustical stimulation. In this embodiment, since residual hearing usually exists on the more apical (lower frequency) part of the cochlea; the electrode array is introduced only until the point where usable hearing begins. An advantage of this technique is that trauma is reduced to a minimum, and that the cochlear mechanics and fluid dynamics (especially at the point where residual hearing is present) are minimally influenced. That is, no portion of the electrode array is positioned adjacent to the apical portion of the cochlea having residual acoustic hearing capability, and the array is thus less likely to interfere with or damage the residual acoustic hearing ability of that portion of the cochlea, while providing electrical stimulation to the basal portion of the cochlea lacking in acoustic hearing capability. Accordingly, surgical trauma to the apical portion of the cochlea may be avoided or minimized by this method.

The optimal insertion depth is determined intra-operatively during the insertion of the electrode array, by investigating the interaction between electrically evoked and acoustically evoked neural responses locally at the point of insertion of the tip of the electrode array. The electrode array is advanced by increments into the cochlea, with the interaction being determined after each incremental advance. When an increase of the interaction strength is determined the insertion is halted, or the electrode may be slightly withdrawn, as the electrode tip has then reached a point where residual hearing exists.

In one embodiment, the interaction between the electrical and acoustical interaction is evaluated as follows. Initially, the most apical electrode records a first compound action potential evoked by application of an electrical stimulus of a given amplitude. The most apical electrode is then used to record a second compound action potential evoked by application of an essentially identical electrical stimulus of the same amplitude, in the presence of a background acoustic noise, preferably a narrow band background acoustic stimulus of a frequency substantially corresponding to the position of the tip electrode, applied to the cochlea. Should the first recorded ECAP and the second recorded ECAP be substantially identical, it can be assumed that the apical electrode of the array is yet to reach the residual functional 'normal hearing' part of the cochlea. However, should the first recorded ECAP and the second recorded ECAP substantially differ, this gives an indication that the presence of masking acoustic noise is evoking a component of neural response which interferes with that evoked by the electrical stimulus. Accordingly, the portion of the cochlea proximal to the apical electrode exhibits residual acoustic hearing capability.

In another embodiment, the frequency where the hearing loss starts is determined using an audiogram. This frequency may then be used in determining the location in the cochlea where the hearing loss starts. For example, in an embodiment, the electrode array is stimulated at its tip at the frequency corresponding to the start of useful hearing. The electrode array is then advanced by increments into the cochlea with the interaction being determined after each incremental advance as with the above-described example. This process is then repeated until the tip of the electrode array reaches the point where the first recorded ECAP and second recorded ECAP substantially differ. This location is then determined to be the location where hearing loss starts. As such, this embodiment differs from the above embodiment in that in this embodiment the frequency is kept constant during insertion.

Figure 6A:
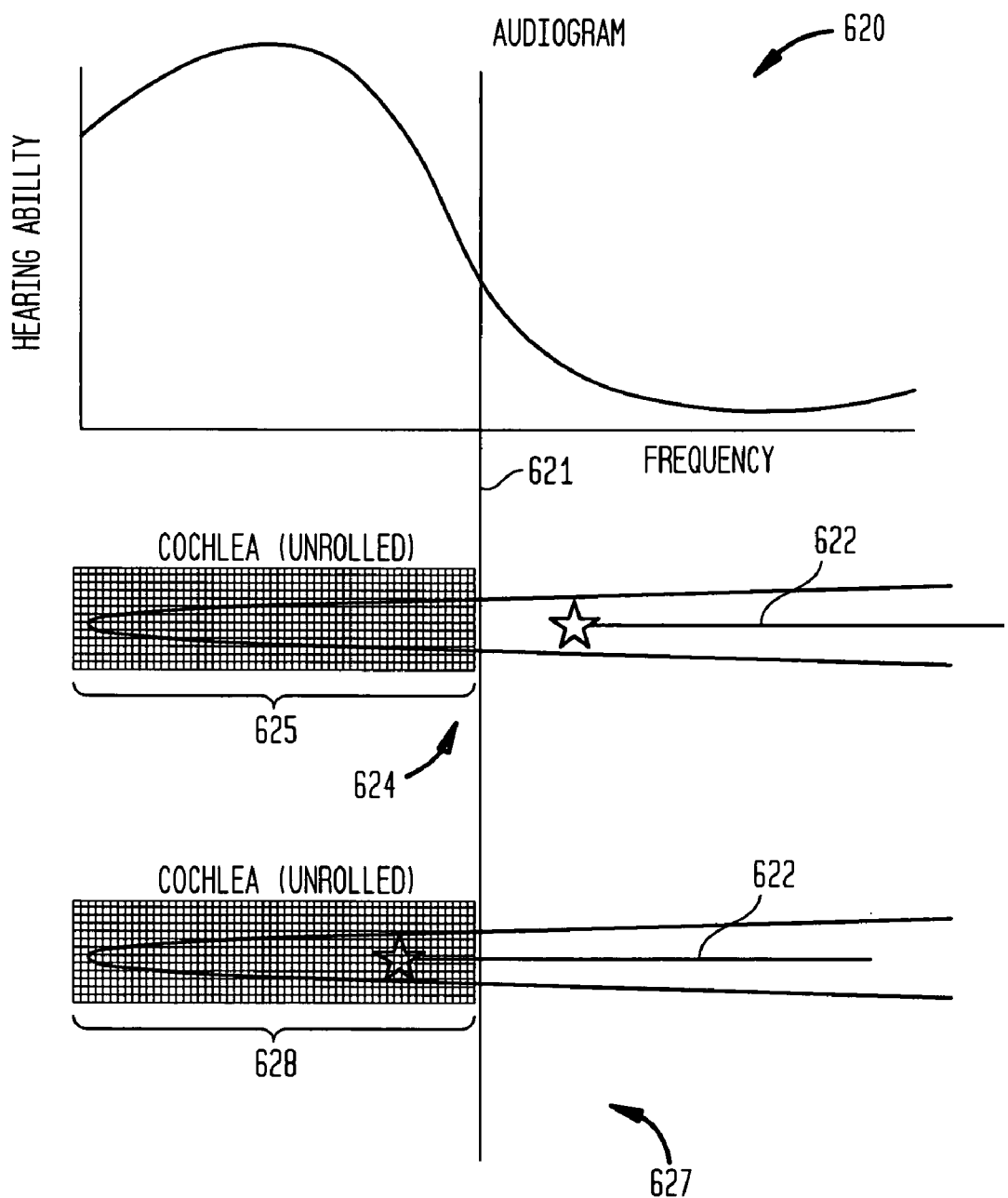
FIG. 6A is a schematic drawing of an implementation of an intra-operative determination of insertion depth of an electrode array in a cochlea having residual acoustic hearing capability.

This procedure is schematically indicated in FIG. 6A. At 620, the recipient's audiogram is displayed, with considerable residual acoustic hearing capability evident in the low frequencies. A cut-off frequency for useful hearing is indicated at line 621, which also marks the location in the unrolled cochlea diagrams 624 and 627 where residual hearing terminates. In the unrolled cochlea, the area 625, 628 of the cochlea that can be measurably masked by a broadband acoustical masking stimulation is indicated by a hashed background. If the electrode array 622 is inserted with the tip in the deaf part of the cochlea (cochlea diagram 624) and an ECAP is recorded at the apical electrode with and without a background acoustical masker, no difference in ECAP amplitude is expected, as indicated by the ECAP graph of FIG. 6B. However, when the electrode array tip is introduced into the acoustically maskable region 628 (corresponding to the region containing residual hearing), as shown in cochlea diagram 627, the ECAP amplitude with a background acoustical masker present varies significantly from that of the unmasked NRT, as indicated by the ECAP graph of FIG. 6C. As illustrated, in this example, the ECAP amplitude with a background acoustical masker present is lower than that of the unmasked NRT. However, in other examples, the ECAP amplitude with a background acoustical masker present may be higher than that of the unmasked NRT.

Figure 6B:
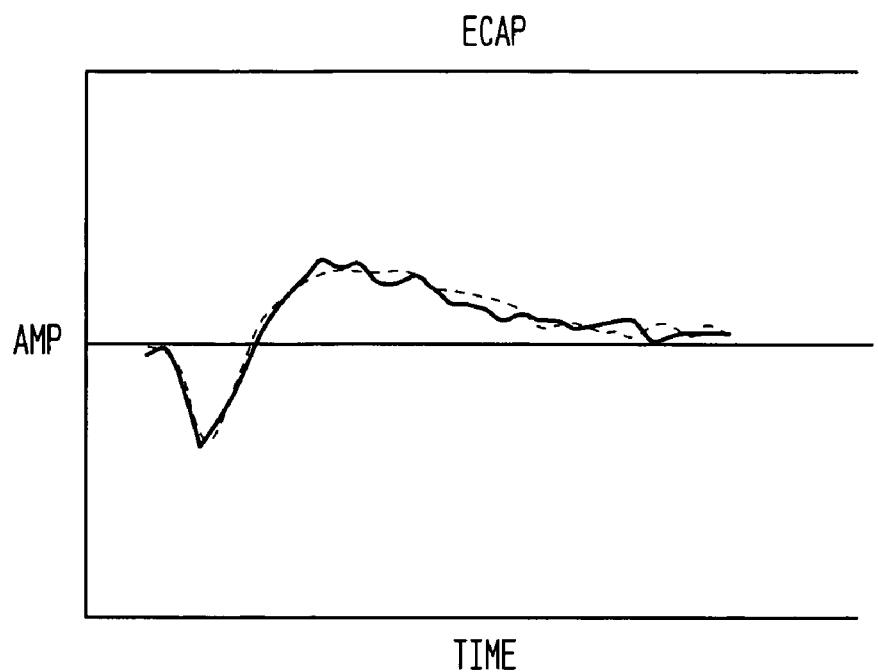
FIGS. 6B and 6C are charts of measured ECAP responses in the implementation of FIG. 6A.
Figure 6C:
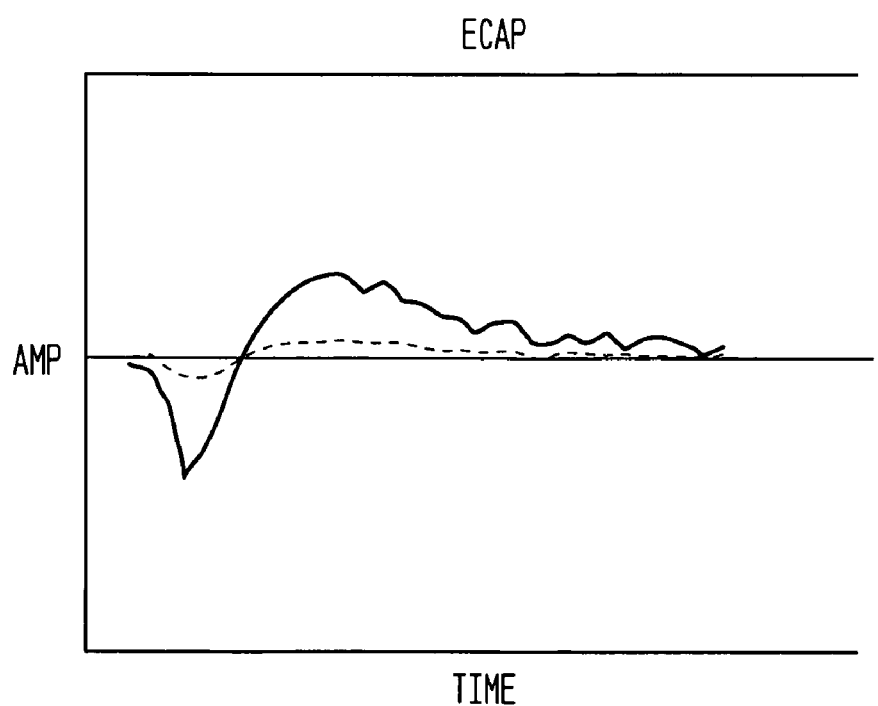
Figure 6D:
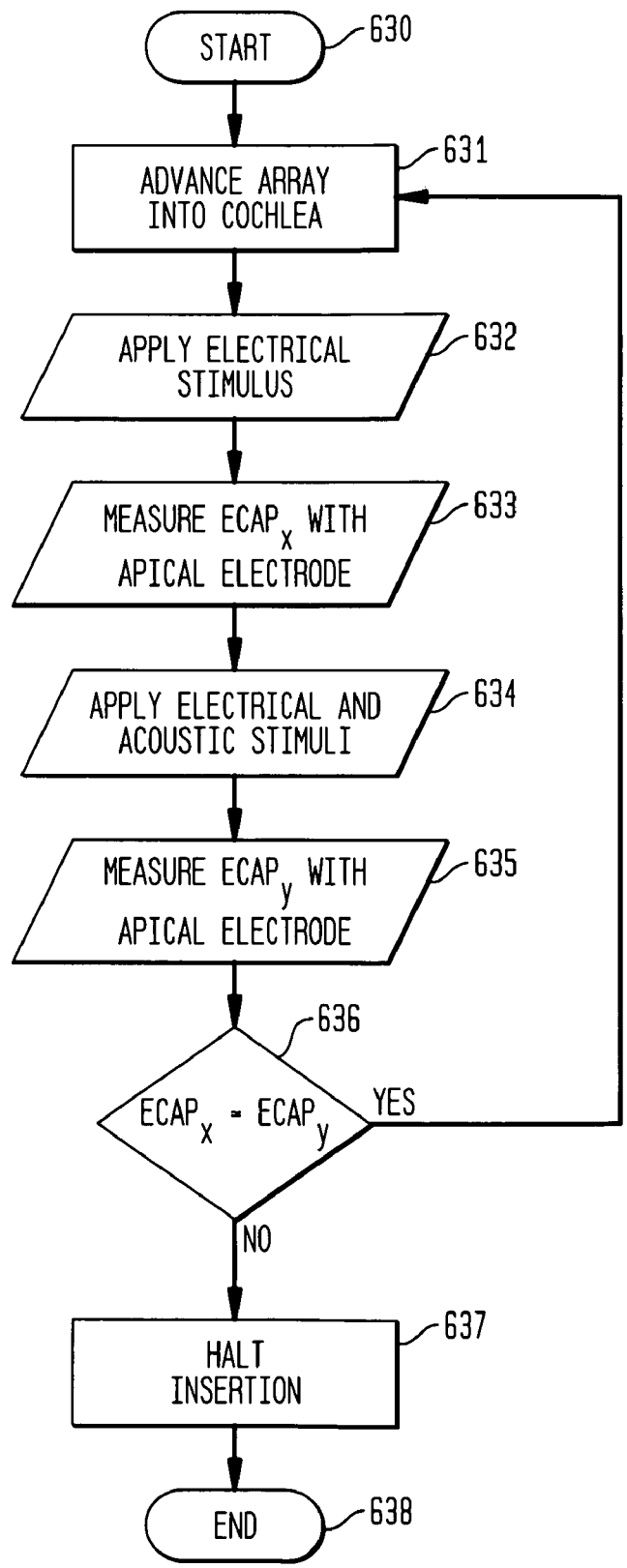
FIG. 6D is a flowchart illustrating the intra-operative process of FIG. 6A.

FIG. 6D is a flowchart of one embodiment of the intra-operative process illustrated in FIGS. 6A to 6C. At block 630 the process commences, after which the electrode array is incrementally advanced by a small amount into the cochlea at block 631. An electrical stimulus is then applied at block 632 in the absence of acoustic stimulation, and a first ECAP denoted $ECAP_x$ is recorded at block 633 using the apical electrode of the array. Subsequently, another electrical stimulus substantially identical to the first stimulus is applied at block 634 simultaneously with an acoustical masking stimulation. The apical electrode is again used at block 635 to measure a second ECAP, denoted $ECAP_y$. At block 636 a comparison is made between $ECAP_x$ and $ECAP_y$. Should $ECAP_x$ be substantially identical to $ECAP_y$, this indicates that the presence of the acoustic masking signal has made no measurable difference to the evoked neural response, thus indicating that there exists no residual acoustic hearing capability at the current position of the apical electrode. Accordingly, the process returns to block 631 at which the electrode array is again incrementally advanced into the cochlea and the process is repeated to determine whether residual acoustic hearing capability exists at the new location of the apical electrode. Should $ECAP_x$ be different to $ECAP_y$, this indicates that the presence of the acoustic masking signal has made a difference to the evoked neural response, thus indicating that residual acoustic hearing capability exists at the present position of the apical electrode. Accordingly, at block 637 the insertion is halted and the process ends at block 638.

In addition to merely determining a point at which residual acoustic hearing capability commences, the process may further include assessing a relative strength of the acoustic hearing capability beyond the threshold, by further inserting the electrode array during the operation for such assessment, and withdrawing the array to its desired post operative position prior to the conclusion of the operation.

In one embodiment the electrode array has a number of electrodes which is significantly greater than the number of channels to be applied by the speech processing scheme to be implemented. Such an electrode is set out in International Publication No. WO 03/003791, the contents of which are hereby incorporated by reference herein. Providing an increased number of electrodes from which to choose for use in applying each signal channel recognizes that, depending on the surgical implantation process, some of the electrodes may be positioned adjacent the apical portion of the cochlea and thus may be inactivated, and/or some of the electrodes may be positioned outside the basal end of the cochlea. Providing an electrode array with sufficiently many electrodes ensures that a sufficient number of the electrodes are adjacent that portion of the cochlea which lacks adequate residual acoustic hearing capability. Such embodiments cater for the application of, for example, all 22 signal channels of an ACE speech processing scheme to only that portion of the cochlea which lacks adequate residual acoustic hearing capability, and provide for finer frequency resolution between signal channels over that portion of the cochlea. To enable such fine frequency resolution, the speech processing scheme implemented is preferably applied to a subset of the audible frequency range tonotopically corresponding to the portion of the cochlea lacking adequate residual acoustic hearing capability.

Alternatively, once a suitable depth of insertion has been determined, a selection may be made of a suitable length electrode to implant. That is, the electrode used for the above determination of suitable insertion depth may be withdrawn, and an electrode of suitable length may be selected and then implanted to the appropriate insertion depth to conclude the surgical procedure. However, care must be taken to avoid or limit damage to the cochlea during such an operative procedure.

Once such partial insertion is complete, a patient map should be determined to allocate suitable frequencies and amplitudes (i.e., C and T levels) to each electrode of the partially inserted array. In particular, in allocating frequency bands to electrodes in the patient map, it is desirable to avoid: (a) the tip electrode(s) applying frequencies which are heard naturally in the more apical part of the cochlea (potentially leading to a "duplicate perception" at that frequency); or (b) the tip electrode frequency being too high and leaving a frequency "gap" which is neither heard naturally nor conveyed electrically.

Figure 7A:
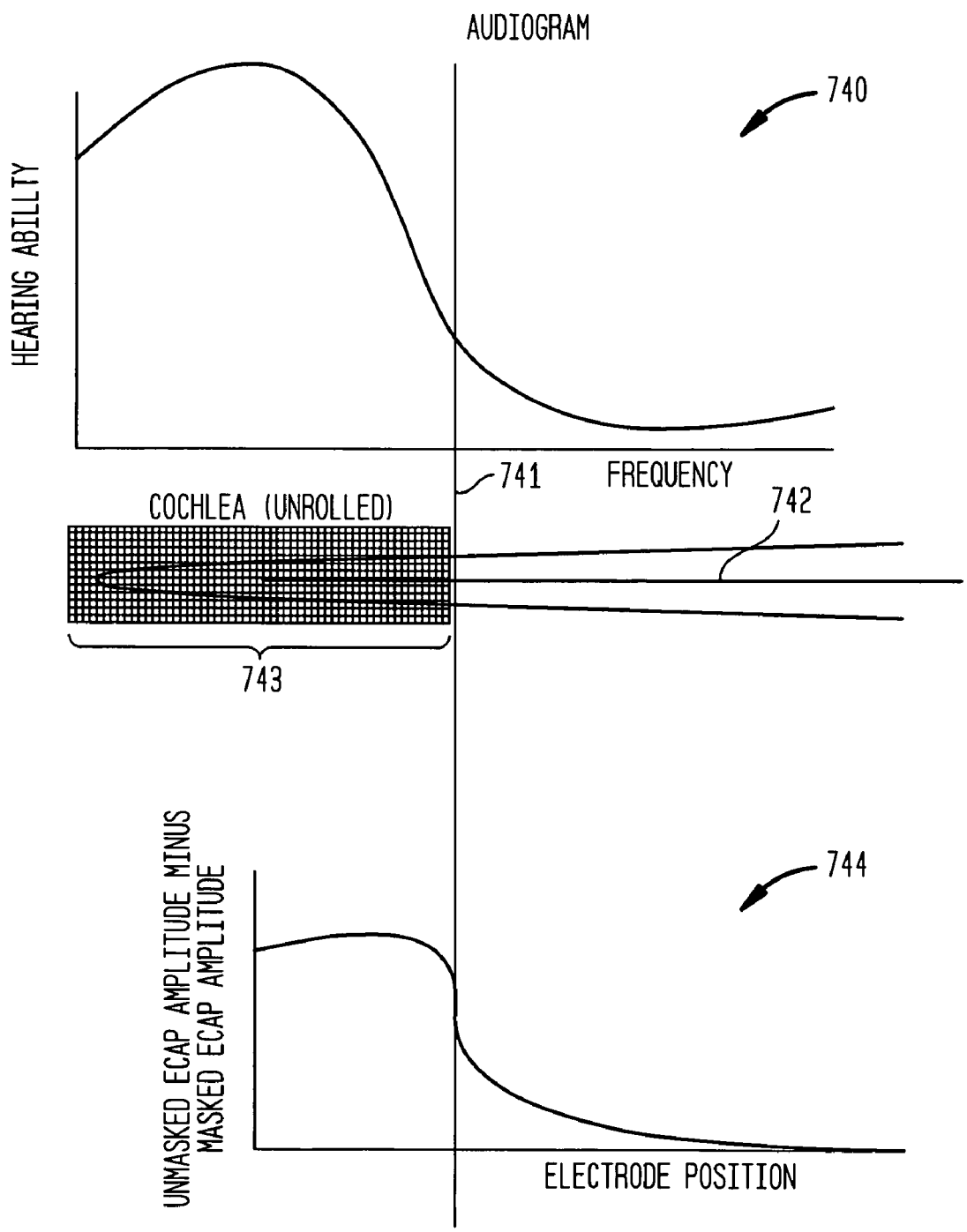
FIG. 7A is a schematic drawing of post operative determination of a patient map for a cochlea having residual acoustic hearing capability.

FIG. 7A illustrates a further embodiment of the present invention, in which the electrode array 742 is inserted fully within the cochlea, and involving a post-operative decision as to which electrodes to inactivate and which to include in the patient map. At 740 the residual hearing capability of the recipient is illustrated, indicating significant residual hearing at low frequencies, up to a threshold 741. Threshold 741 also indicates a position along the cochlea at which the residual hearing portion 743 terminates. In this embodiment, only a subset of electrodes are active in the map. Thus the natural pathway for delivery of acoustic sound is utilized to the extent that it still exists, while electrical stimuli are provided to convey sound information which is no longer perceptible by the cochlea and/or to supplement sound information only partially perceptible by the cochlea. Accordingly, the implant recipient will receive natural sounding percepts from those portions of the cochlea having hearing capability. This technique is advantageous in that when the hearing loss progresses over time, the patient map can be adjusted accordingly, without the need for further surgical intervention.

However, once again, in order to determine an optimal patient map it is desirable to assess the interaction between electrical and acoustic stimulation along the cochlea, in order to determine the physical point 741 in the cochlea at which electrical stimulation begins to interfere with (useful) acoustical stimulation.

Figure 7B:
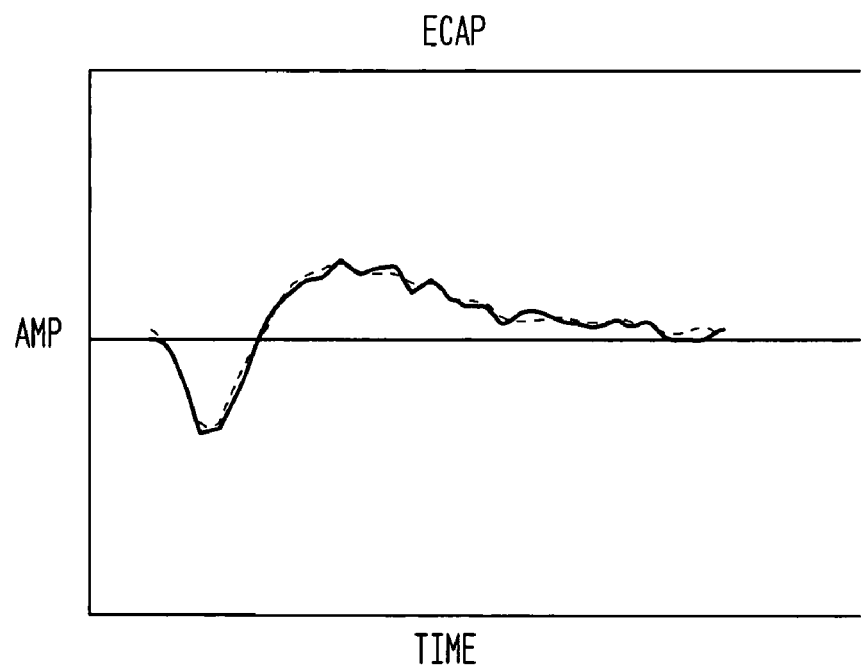
FIGS. 7B and 7C are charts of measured ECAP responses in the implementation of FIG. 7A.
Figure 7C:
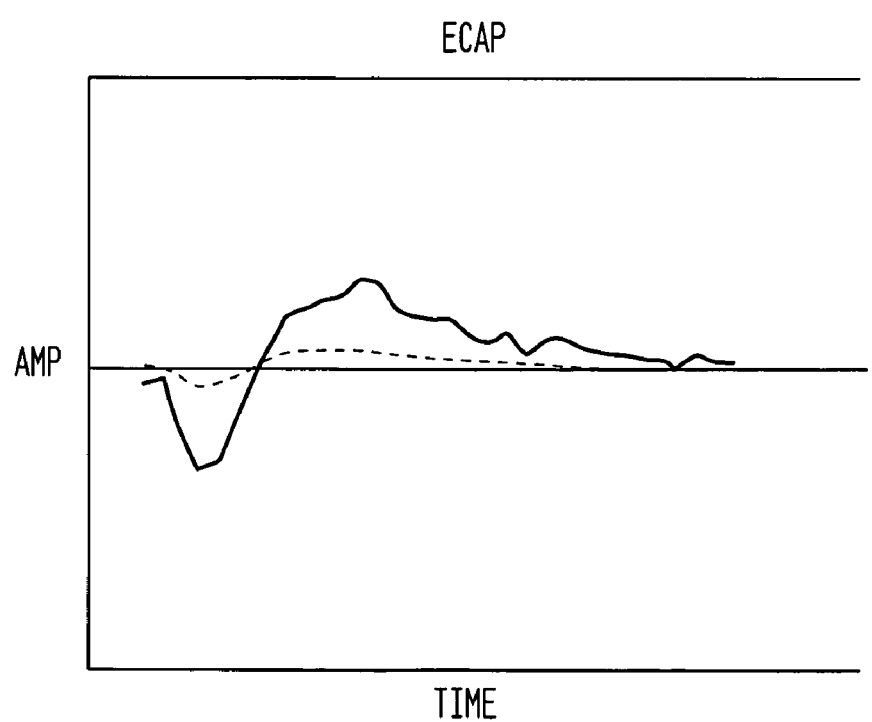
Figure 7D:
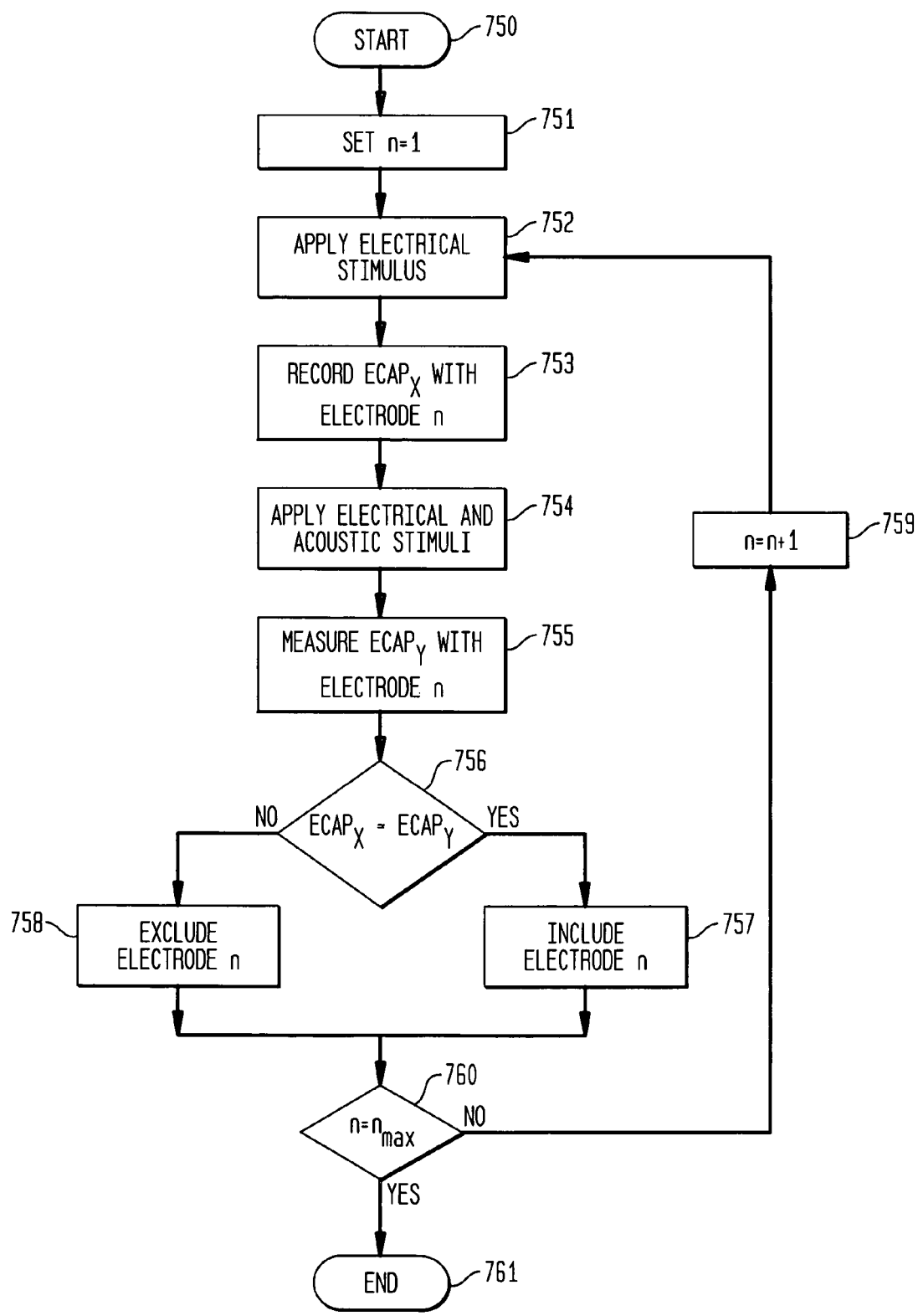
FIG. 7D is a flowchart illustrating the post-operative process of FIG. 7A.

FIG. 7D is a flowchart illustrating a process for determining a suitable patient map for the implant configuration set out in FIGS. 7A through 7C. At block 750 the process begins, and at block 751 a sense electrode is set to be a first electrode of the array. At block 752 an electrical stimulus is applied in the absence of any acoustic stimulation, and at block 753 the first electrode is used to sense and record a first ECAP, denoted $ECAP_x$, evoked by the electrical stimulus applied at block 752.

Subsequently, at block 754 a substantially identical electrical stimulus is applied, and in addition a simultaneous acoustic stimulus is applied having at least a frequency component tonotopically corresponding to the position of electrode n. At block 755 the same (first) electrode is used to sense and record a second ECAP, denoted $ECAP_y$, evoked by the simultaneous electrical and acoustic stimuli applied at block 754. Alternatively, as discussed above, the frequency of the acoustic stimulus may be set as the frequency corresponding to the point where hearing loss begins as, for example, determined by an audiogram. This frequency may then be kept constant as the electrode array is incrementally inserted into the cochlea.

A comparison is then made at block 756 of $ECAP_x$ and $ECAP_y$. Should $ECAP_x$ be substantially identical to $ECAP_y$, as shown in FIG. 7B, then this indicates that the presence or absence of acoustic stimulation has made no measurable difference, and thus indicates that residual hearing capability does not exist proximal to the first electrode. In this event the first electrode is at block 657 included in the patient map in order that the first electrode is used to apply electrical stimuli to the cochlea to convey sound information tonotopically corresponding to the position of that electrode, due to the natural hearing no longer conveying such sound information. Alternatively, should the comparison made at block 756 reveal that $ECAP_x$ is not substantially identical to $ECAP_y$, as shown in FIG. 7C, then this indicates that the presence of the acoustic masking stimulus has made a difference to the evoked neural response, thus indicating that residual acoustic hearing capability exists proximal to the first electrode. In this event, electrode n (n=1) is excluded from the patient map at block 758. This process is repeated for all electrodes of the array by incrementing n at block 759, unless all electrodes have been assessed, in which case $n=n_{max}$ and decision 760 causes the process to end at block 761.

It is to be appreciated that the interaction between electrical and acoustic stimuli may be assessed in an alternate manner. For instance, the interaction may alternatively or additionally be assessed by applying a narrowband acoustic stimulus and recording an evoked CAP using a sense electrode tonotopically corresponding to the frequency of the narrowband stimulus. Then a substantially identical narrowband acoustic stimulus may be applied simultaneously with a masking electrical stimulation (for example applied by an electrode adjacent to the sense electrode), and again recording an evoked CAP. This process may be repeated for acoustically applied frequencies throughout the normal hearing range with a tonotopically corresponding sense electrode for each frequency.

Once an assessment has been made of the interaction between acoustic and electrical stimuli along the cochlea an "interaction map" of the cochlea may be produced, of the type illustrated by audiogram 744 in FIG. 7A. Such an interaction map may be used in conjunction with conventional audiometry to determine a suitable cut off frequency 741, to determine where in the cochlea electrical stimulation does not influence the acoustic hearing capability, to map the processor on the non interacting electrodes only, using a frequency allocation table (FAT) that only stimulates those frequencies that are not represented and conveyed by the auditory system naturally.

The audiogram shown in FIG. 7A is representative of the most common type of hearing loss in which a cochlea loses hearing ability at high frequencies. However it is to be appreciated that, for a cochlea where hearing capability is deficient in alternate ways, such as the loss of low frequency capability, the embodiment of FIGS. 3A to 3D can still be used to provide for electrical supplementation of residual acoustic hearing capability, wherever that capability may exist in the operating frequency range.

Figure 8:
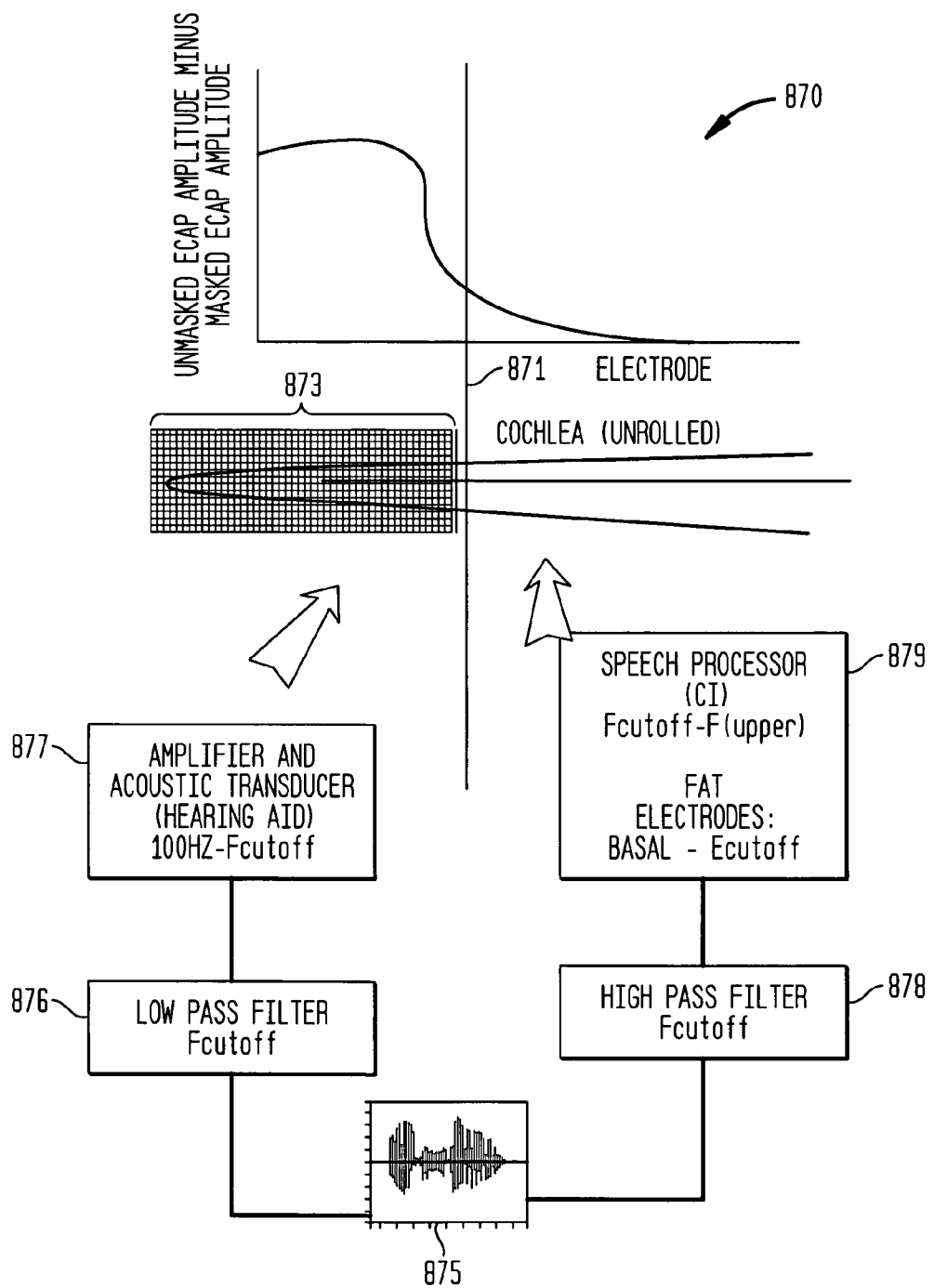
FIG. 8 is a schematic drawing of mapping a device using both electrical and acoustic modes of stimulation.

The embodiments shown in FIGS. 6A to 6D and FIGS. 7A to 7D may each be incorporated into a bimodal hearing prosthesis of the present invention. FIG. 8 illustrates a bimodal device in accordance with the embodiment of FIGS. 2, and 7A to 7D. Once the cut off frequency 871 (corresponding to "cut-off electrode") has been determined, whether by the method set out in FIG. 6B or FIG. 7B, electrical stimuli may be applied in one mode above that frequency, and acoustic stimuli may be applied in the other mode below that frequency. At 870 the determined masking profile is displayed. Portion 873 of the cochlea is where residual acoustic hearing capability exists. Knowing the acoustic cut off frequency of that residual hearing, and knowing which electrode is located at the cut off boundary 871 in the cochlea, it is possible to separate detected sound 875 into two components. Below the cut-off frequency the sound is amplified and applied to the ear acoustically, by low pass filter 876 and transducer 877. The portion of the detected sound above the cut off frequency is processed by a high pass filter 878 and a cochlear implant speech processor 879 and mapped to those electrodes that are in the non-functional part of the cochlea. In this way the accessible frequency range is optimized, and the interaction between acoustic and electric hearing is minimized. It should be noted that the speech processor 879 of FIG. 8 corresponds to the electrical signal analyzer 208 of FIG. 2, and as discussed above, may include a delay circuit for ensuring that both acoustic and electrical stimulations are substantially simultaneously delivered to the cochlea (i.e., the implant recipient does not perceive a delay (or a substantial delay) between the two signals).

It is to be appreciated that electrical stimulation may also be used to supplement the application of acoustic stimulation to the portion 873 of the cochlea having partial residual hearing. Such supplemented electrical stimulation may be mapped to have a strength to complement the residual audiogram strength along the cochlea in region 873. Such embodiments provide for a transition from purely acoustic hearing at the apical end of the cochlea to purely electrical stimulation at the basal end of the cochlea, with a central portion of the cochlea having both acoustic and electrical stimulation applied thereto and the central portion of the cochlea being relied upon to convey both acoustic and electrical stimulation. Should the residual hearing be inadequate, electrical stimulation may be applied by all electrodes of the array, with apical electrodes being mapped to have a strength which complements the residual acoustic hearing strength of the portion 873 of the cochlea.

Further, high pass filter 878 may be excluded where an appropriate patient map exists in speech processor 879 which inactivates apical electrodes of the array.

Figure 9:
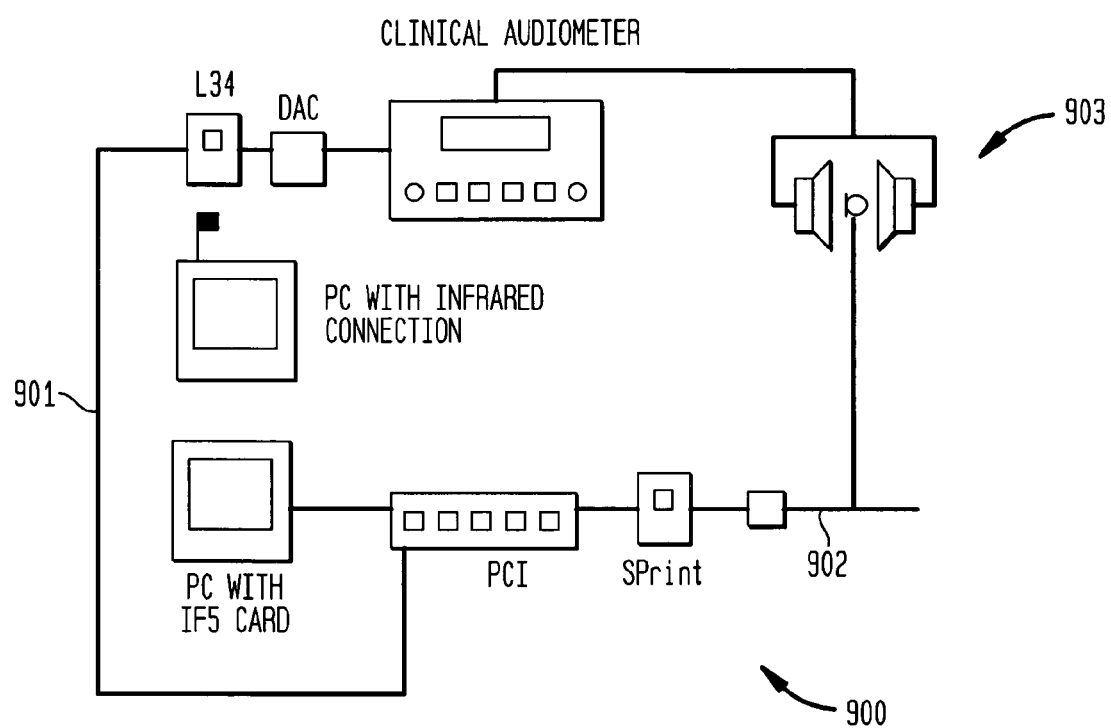
FIG. 9 illustrates a system for clinical testing and/or fitting of a cochlear implant to be used to supplement the residual acoustic hearing capability of a cochlea.

FIG. 9 illustrates a system 900 for clinical testing and/or fitting of a cochlear implant 902 to be used to supplement the residual acoustic hearing capability of a cochlea. A trigger signal 901 is applied electrically via the electrode array of the cochlear implant 902 and acoustically via headphones 903. The trigger signal in the system 900 illustrated is generated by a personal computer (PC) with infrared connection via L34, a digital to analogue converter and a clinical audiometer to the headphones 903, and via L34, PCI and a Sprint speech processor to the cochlear implant 902. The PC-infrared-L34-DAC connection may alternatively be provided by a triggerable signal generator with analogue output. For example, system 900 may be used in obtaining intra-operative NRT recordings of both electrical and acoustic stimuli to determine suitable array insertion depths.

System 900 may further be used to determine suitable delays to be introduced in order to ensure accurate timing of the delivery of electrical stimulations relative to acoustic stimulations. Such an embodiment recognizes that, due to the differing pathways for delivery of acoustic stimuli and electric stimuli to the cochlea, neural responses caused by electrical stimuli may be mistimed relative to neural responses caused by acoustic stimuli. In certain circumstances such as mistiming may reduce the intelligibility of speech or otherwise have an undesirable effect on sound perception by the user. Should neural responses to acoustic stimuli arise after neural responses to electrical stimuli, for instance due to the time of transmission from the outer ear, through the middle ear, into the inner ear and via the basilar membrane, an appropriate delay in applying electrical stimulation is preferably introduced. The timing of the electrical stimulations relative to the timing of the acoustic stimulations may be optimized by use of neural response measurements, such as those discussed above, and appropriate adjustments are preferably made to the delay in delivery of electrical stimuli by for example adjusting the delays of delay circuits included in the electrical signal delivery path and/or the acoustic signal delivery path such as was discussed above with regards to FIGS. 2-4.

Uses of embodiments of the present invention include research and auditory states monitoring, in which a bimodal speech processor could generate an acoustical stimulus and record the resulting CAP, comparing it to previous CAP recordings. If the recipient's hearing is further deteriorating and refitting is needed, this could be detected automatically by such a system. Embodiments of the present invention may further provide for high resolution audiogram imaging in combination with classical audiometry, and may provide for detection of double peaks in the neural response.

It is to be appreciated that determination of tonotopic cochlear positions in this document is not limited to a classical determination of cochlear position relative to frequency or pitch. In particular, it is to be appreciated that existing formulae to relate cochlear position to pitch, such as Greenwood's formulae (J. Acoust. Soc. Am. Vol 87, No 6, June 1990) may not always be sufficiently accurate in relation to tonotopic cochlear positions for electrical stimuli.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the invention as shown in the specific embodiments without departing from the spirit or scope of the invention as broadly described. The present embodiments are therefore, to be considered in all respects as illustrative and not restrictive.

All documents, patents, journal articles and other materials cited in the present application are hereby incorporated by reference herein.

What is claimed is:

1. A method of electrically and acoustically stimulating a cochlea, comprising:
providing an electrical signal delivery path to the cochlea, for processing a first frequency sub-range of a detected sound signal for electric stimulation of the cochlea;
providing an acoustic signal delivery path to the cochlea for a second frequency sub-range corresponding to a residual natural hearing capability of the cochlea; and
imposing a delay on the electrical signal delivery path, to provide for delivery of the electrical stimulation to the cochlea at a desired time relative to a time of arrival of acoustic stimuli at the cochlea,
wherein acoustic stimuli arriving at the cochlea and the electrical stimulation delivered to the cochlea at the desired time substantially simultaneously stimulate the cochlea.

2. The method of claim 1, wherein the acoustic signal delivery path comprises an acoustic sound processor for processing a second frequency sub-range of the detected sound signal; and the method further comprising:
acoustically delivering the processed acoustic sound signal to the cochlea.

3. The method of claim 1, wherein the electrical signal delivery path comprises a plurality of electrical channels, wherein the first frequency sub-range of the detected sound signal is divided into a plurality of frequency bands, with one frequency band processed in each electrical channel.

4. The method of claim 3, wherein a channel-specific delay is applied to each electrical channel.

5. The method of claim 4, wherein the channel-specific delay of each electrical channel is configured to delay low frequency electrical channels for a time longer than that by which high frequency electrical channels are delayed, to mimic the time taken for sound to travel from a basal region of the cochlea tonotopically corresponding to the high frequency channels to a more apical region of the cochlea tonotopically corresponding to the low frequency channels.

6. The method of claim 5, wherein the first frequency sub-range comprises a portion or portions of the audible frequency spectrum in respect of which active stimulus electrodes have been tonotopically positioned proximal to the cochlea.

7. The method of claim 5, wherein the first frequency sub-range comprises a high frequency portion of the audible frequency spectrum, where active electrodes have been positioned proximal to a basal portion of the cochlea.

8. The method of claim 1, wherein the delay is substantially equal to a difference between the time taken for a signal to travel along the electrical signal delivery path and the time taken for a signal to travel along the acoustic signal delivery path, such that imposing the delay provides for the cochlea to be substantially simultaneously stimulated electrically and acoustically in response to the detected sound signal.

9. The method of claim 8, wherein the imposed delay is clinically configurable.

10. The method of claim 8, wherein the imposed delay is field configurable.

11. The method of claim 1, further comprising sensing a neural response to determine a relative timing of delivery of electrical stimuli and acoustic stimuli.

12. The method of claim 1, wherein a cochlear implant is utilized to provide the electrical signal delivery path to the cochlea.

13. A method of electrically and acoustically stimulating a cochlea, comprising:
providing an electrical signal delivery path to the cochlea, for processing a first frequency sub-range of a detected sound signal for electric stimulation of the cochlea;
providing an acoustic signal delivery path to the cochlea for a second frequency sub-range corresponding to a residual natural hearing capability of the cochlea; and
imposing a delay on at least one of the acoustic signal delivery path and the electrical signal delivery path, to provide for delivery of the electrical stimulation to the cochlea at a desired time relative to a time of arrival of acoustic stimuli at the cochlea, wherein
acoustic stimuli arriving at the cochlea and the electrical stimulation delivered to the cochlea at the desired time substantially simultaneously stimulate the cochlea,
the acoustic signal delivery path comprises an acoustic sound processor for processing a second frequency sub-range of the detected sound signal,
the method further comprises acoustically delivering the processed acoustic sound signal to the cochlea, and
the acoustic processing comprises a plurality of acoustic channels.

14. The method of claim 13, wherein a channel-specific delay is imposed upon each acoustic channel.

15. The method of claim 13, wherein a channel-specific gain is applied to each acoustic channel.

16. A method of fitting a cochlear prosthesis to a cochlea having residual acoustic hearing capability such that the cochlea can be electrically stimulated via an electrical signal delivery path for processing a first frequency sub-range of a detected sound signal for electrical stimulation of the cochlea, and acoustically stimulated via an acoustic signal delivery path for a second frequency sub-range corresponding to a residual natural hearing capability of the cochlea, the method comprising:
configuring a delay to be imposed on the electrical signal delivery path, to provide for delivery of the electrical stimulation to the cochlea at a desired time relative to a time of arrival of acoustic stimuli at the cochlea, and
providing the configured delay for use in fitting the cochlear prosthesis including electrically stimulating the cochlea via a provided electrical signal delivery path to the cochlea for processing the first frequency sub-range of the detected sound signal for electrical stimulation of the cochlea, and acoustically stimulating the cochlea via a provided acoustic signal delivery path to the cochlea for the second frequency sub-range corresponding to the residual natural hearing capability of the cochlea,
wherein acoustic stimuli arriving at the cochlea and the electrical stimulation delivered to the cochlea at the desired time substantially simultaneously stimulate the cochlea.

17. The method of claim 16, wherein the acoustic signal delivery path comprises an acoustic sound processor for processing a second frequency sub-range of the detected sound signal, the method further comprising acoustically delivering the processed acoustic sound signal to the cochlea.

18. The method of claim 16, wherein the delay is configured to be imposed upon the electrical signal delivery path.

19. The method of claim 18, wherein the electrical signal delivery path comprises a plurality of electrical channels, wherein the first frequency sub-range of the detected sound signal is divided into a plurality of frequency bands, with one frequency band processed in each electrical channel.

20. The method of claim 16, wherein the electrical signal delivery path is formed by a cochlear implant.

21. A method of fitting a cochlear prosthesis to a cochlea having residual acoustic hearing capability such that the cochlea can be electrically stimulated via an electrical signal delivery path for processing a first frequency sub-range of a detected sound signal for electrical stimulation of the cochlea, and acoustically stimulated via an acoustic signal delivery path for a second frequency sub-range corresponding to a residual natural hearing capability of the cochlea, the method comprising:

configuring a delay to be imposed on at least one of the acoustic signal delivery path and the electrical signal delivery path, to provide for delivery of the electrical stimulation to the cochlea at a desired time relative to a time of arrival of acoustic stimuli at the cochlea, wherein acoustic stimuli arriving at the cochlea and the electrical stimulation delivered to the cochlea at the desired time substantially simultaneously stimulate the cochlea, the acoustic signal delivery path comprises an acoustic sound processor for processing a second frequency sub-range of the detected sound signal, the method further comprises acoustically delivering the processed acoustic sound signal to the cochlea, and the acoustic processing comprises a plurality of acoustic channels.

22. The method of claim 21, further comprising configuring a channel-specific delay to be imposed upon each acoustic channel.

23. A hearing prosthesis comprising:

an electrical signal analyzer configured to process a first frequency sub-range of a detected sound signal for electric stimulation of the cochlea; and a delay circuit configured to impose a delay on an electrical signal delivery path to provide for delivery of the electrical stimulation to the cochlea at a desired time relative to a time of arrival of acoustic stimuli at the cochlea, wherein acoustic stimuli arriving at the cochlea and the electrical stimulation delivered to the cochlea at the desired time substantially simultaneously stimulate the cochlea.

24. The hearing prosthesis according to claim 23, further comprising:

an acoustic signal analyzer configured to process a second frequency sub-range of the detected sound signal, and acoustically deliver the processed acoustic sound signal to the cochlea.

25. The hearing prosthesis of claim 24, wherein the second frequency sub-range corresponds to a residual natural hearing capability of the cochlea.

26. The hearing prosthesis of claim 23, wherein the delay circuit is configured to impose a delay upon the electrical signal delivery path.

27. The hearing prosthesis of claim 23, wherein the electrical signal delivery path is formed at least in part by an electrode array of the cochlear prosthesis.

28. A hearing prosthesis comprising:

an electrical signal analyzer configured to process a first frequency sub-range of a detected sound signal for electric stimulation of the cochlea;

a delay circuit configured to impose a delay on an electrical signal delivery path to provide for delivery of the electrical stimulation to the cochlea at a desired time relative to a time of arrival of acoustic stimuli at the cochlea; and an acoustic signal analyzer configured to process a second frequency sub-range of the detected sound signal, and acoustically deliver the processed acoustic sound signal to the cochlea, wherein the hearing prosthesis is configured such that acoustic stimuli arriving at the cochlea and the electrical stimulation delivered to the cochlea at the desired time substantially simultaneously stimulate the cochlea, and the acoustic signal analyzer is further configured to process a plurality of acoustic channels.

* * * * *